US009751956B2

(12) United States Patent
Chuang et al.

(10) Patent No.: US 9,751,956 B2
(45) Date of Patent: Sep. 5, 2017

(54) METHOD OF USING SUPERCRITICAL FLUID TECHNOLOGY TO SEPARATE AND PURIFY FUNCTIONAL COMPONENTS OF ANTRODIA CAMPHORATA

(71) Applicant: Ultra-Microrigin Biomedical Technology Co., Ltd., Zhubei (TW)

(72) Inventors: Ming-Hsi Chuang, Zhubei (TW); Chu-Ting Lin, Zhubei (TW); I-Lung Yu, Zhubei (TW); Lin-Hsiang Chuang, Zhubei (TW)

(73) Assignee: ULTRA-MICRORIGIN BIOMEDICAL TECHNOLOGY CO., LTD., Zhubei (TW)

( * ) Notice: Subject to any disclaimer, the term of this patent is extended or adjusted under 35 U.S.C. 154(b) by 14 days.

(21) Appl. No.: 14/828,658

(22) Filed: Aug. 18, 2015

(65) Prior Publication Data

US 2016/0257768 A1 Sep. 8, 2016

(30) Foreign Application Priority Data

Mar. 6, 2015 (TW) ............................. 104107291 A

(51) Int. Cl.

| | |
|---|---|
| ***C08B 37/00*** | (2006.01) |
| ***C07J 75/00*** | (2006.01) |
| ***C07J 63/00*** | (2006.01) |
| ***C07J 9/00*** | (2006.01) |

(52) U.S. Cl.

CPC .......... *C08B 37/0003* (2013.01); *C07J 9/005* (2013.01); *C07J 63/008* (2013.01); *Y02P 20/544* (2015.11)

(58) Field of Classification Search

CPC ...... C08B 37/0003; C07J 9/005; C07J 63/008

See application file for complete search history.

(56) References Cited

U.S. PATENT DOCUMENTS

| | | | |
|---|---|---|---|
| 7,994,158 | B2 | 8/2011 | Chen et al. |
| 2010/0210869 | A1 | 8/2010 | Wu et al. |
| 2010/0227404 | A1 | 9/2010 | Wu et al. |

OTHER PUBLICATIONS

Lien et al., Molecules, 2014, 19, p. 9033-9050, published Jun. 27, 2014.*

Liang et al., J. Taiwan Inst. Chem. Eng., 2014, 45, p. 1225-1232, Available online Nov. 20, 2013.*

* cited by examiner

*Primary Examiner* — Jonathan S Lau

(74) *Attorney, Agent, or Firm* — Jackson IPG PLLC; Demian K. Jackson

(57) ABSTRACT

A method of using supercritical fluid technology to separate and purify the functional components of *Antrodia cinnamomea* is described. Triterpenoids and polysaccharides of *Antrodia cinnamomea* are extracted from a fractionation tank containing extract of *Antrodia cinnamomea* and supercritical solvent at a set temperature and pressure. The extracted functional components and supercritical solvent are then continuously fed into three separating tanks at a set temperature and a pressure below that of the aforesaid pressure to obtain various functional components of triterpenoids and polysaccharides from the *Antrodia cinnamomea* feed in each separating tank.

3 Claims, 4 Drawing Sheets

METHOD OF USING SUPERCRITICAL FLUID TECHNOLOGY TO SEPARATE AND PURIFY FUNCTIONAL COMPONENTS OF ANTRODIA CAMPHORATA

BACKGROUND OF INVENTION

1. Field of the Invention

The present invention relates to a technology of separating and purifying the functional components of *Antrodia cinnamomea*. More specifically, the invention relates to the use of supercritical fluid technology to separate and purify the functional components of *Antrodia cinnamomea*.

2. Description of Related Art

*Antrodia cinnamomea* is a parasitic fungus which only grows on the inner heartwood wall of lauraceae plants, such as *Cinnamomum kanehirae*). Because of its antioxidant property, blood pressure lowering effect, and immune enhancing activity, *Antrodia cinnamomea* It can be used not only for food but has extensively been utilized in the treatment of drug poisoning, diarrhea, abdominal pain, high blood pressure, and cancer.

The active components of *Antrodia cinnamomea* include triterpenoids, polysaccharides, adenosine, vitamin, protein, peptide, nucleic acid. The triterpenoids can mainly be divided into ergostane-type triterpenoids (zhankuic acid A, zhankuic acid C, antcin A, and antcin K) and lanostane-type triterpenoids (dehydroeburicoic acid and dehydrosulphurenic acid). Previous research showed that the antcin A in the extract obtained from the fruiting body of *Antrodia cinnamomea* could suppress the activity of leukemia cells in rats and zhankuic acid A and zhankuic acid C exhibited strong antitumor effects on cancer cells. Dehydrosulphurenic acid and dehydroeburicoic acid have also been demonstrated to possess antineoplastic activity, which could enhance apoptosis of cancer cells without affecting normal human cells. The presence of polysaccharides components in *Antrodia cinnamomea* has also experimentally proven.

The conventional methods of extracting the active components triterpenoids and polysaccharides from *Antrodia cinnamomea*, such as those described in the China patent CN 102614195 A and the United States Patent 20100210869 A1, use ethanol solution, normal hexane solution, and ethyl acetate solution to extract the ergostane-type and lanostane-type triterpenoids from the fruiting body of *Antrodia cinnamomea*. The U.S. Pat. No. 7,994,158 B2 was the first to use water or organic solvent (for example, ethyl acetate, hexane, alcohols, and chloroform) extraction. The water or organic solvent extracts obtained then is concentrated and purified using silica gel and Sephadex. The United States Patent 20100227404 A1 describes a method that use ethyl acetate, ethanol, and water to extract polysaccharides from the fruiting body of *Antrodia cinnamomea*. In addition, the Taiwan patent 1299665 uses ethanol to extract polysaccharides from the mycelium of *Antrodia cinnamomea*.

From the above mentioned it can be concluded that the conventional methods of extracting triterpenoids and polysaccharides from *Antrodia cinnamomea* are time-consuming and require a large amount of organic solvent. Unwanted chemical reactions may occur between the organic solvent and the functional components during the extraction process. In addition, the removal of solvent using heat evaporation after the extraction may have detrimental effects on part of the functional components. Furthermore, there are concerns over trace amount of solvent may remain in the final product. Therefore, it is clear that there is still room for improvement.

SUMMARY OF THE INVENTION

The main aim of the present invention is to provide a method using supercritical fluid technology to separate and purify the functional components of *Antrodia cinnamomea*. The functional components of triterpenoids and polysaccharides can directly be extracted from *Antrodia cinnamomea* without the need for complicated solvent removal and concentration and separation processes. In addition, there are no safety concerns with solvent remaining in the final product. Moreover, the cost of the method is low and the activity of the biologically active constituents of *Antrodia cinnamomea* can be maintained. The method is environmentally friendly, safe, and practical.

Therefore, in order to attain the aforesaid aim, the present invention provides a method using supercritical fluid technology to separate and purify the functional components of *Antrodia cinnamomea*. Triterpenoids and polysaccharides of *Antrodia cinnamomea* are extracted from a fractionation tank containing extract of *Antrodia cinnamomea* and supercritical solvent at a set temperature and pressure. The extracted functional components and supercritical solvent are then continuously fed into three separating tanks at set temperatures and pressures below that of the aforesaid pressure to obtain various functional components of triterpenoids and polysaccharides from the *Antrodia cinnamomea* feed in each separating tank.

BRIEF DESCRIPTION OF THE DRAWINGS

A preferred embodiment of the present invention is detailed in the figures as follows.

DETAILED DESCRIPTION OF THE PREFERRED EMBODIMENT

Figure 1:
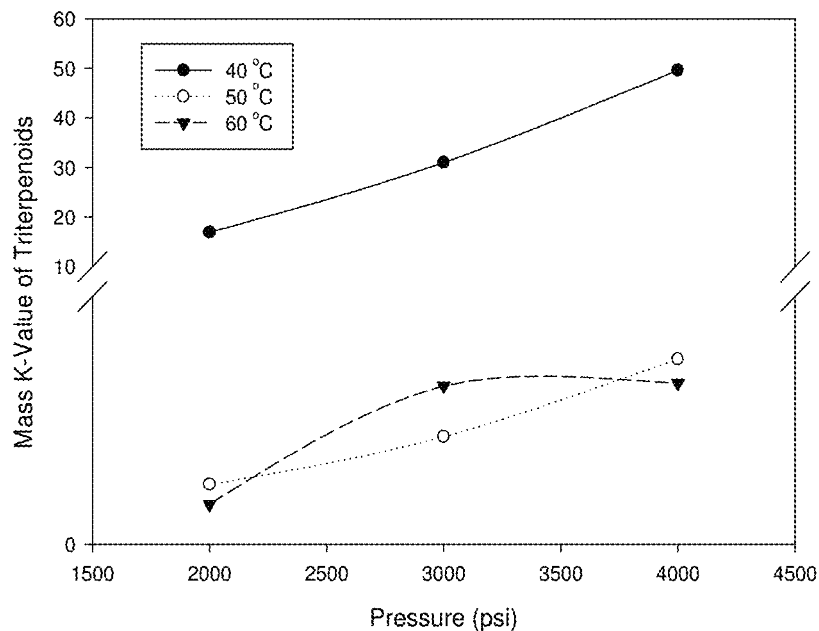
FIG. 1 is an analytic chart of pressure and K-value of *Antrodia cinnamomea* triterpenoids of a preferred embodiment of the present invention.

A preferred embodiment of the present invention uses supercritical fluid technology to separate and purify the functional components of *Antrodia cinnamomea*. First, 1 to 2 Kg *Antrodia cinnamomea* powder preparation (can be the fruiting body, mycelium, dish culture, or solid culture of *Antrodia cinnamomea*), is mixed with ethanol in ratio of 1:5 to 10 (weight per volume). The mixture is centrifugated to obtain the *Antrodia cinnamomea* feed. The *Antrodia cinnamomea* feed is introduced into a fractionating tank for separation under the operating conditions of temperature at 40° C. to 60° C., a flow velocity of supercritical fluid (SC—$CO_2$/ethanol solvent) at 3 L/hr to 9 L/hr, and a

*Antrodia cinnamomea* feed flow velocity at 1 L/hr to 3 L/hr. Triterpenoids and polysaccharides contents from *Antrodia cinnamomea* are obtained separately from the top and the bottom of the fractionating tank. The fractionating tank is a stainless steel tank with an inside diameter of 36 mm and a height of 1000 mm, which is filled with stainless steel single sheet.

Next, the functional components triterpenoids and polysaccharides of *Antrodia cinnamomea* obtained from the supercritical fluid extraction are conveyed continuously through three separating tanks at 40° C. or 60° C., at pressures of 3000 psi, 2000 psi, and 1000 psi in the first, second, and third separating tank, respectively. Raffinate is obtained at the bottom of the fractionating tank. In other words, the functional components of triterpenoids and polysaccharides in *Antrodia cinnamomea* feed are obtained from the three separating tanks as: separated product 1 (F1), separated product 2 (F2), and separated product 3 (F3). The three separating tanks are made in stainless steel with an inside diameter of 36 mm and a height of 500 mm.

Different operating conditions (different pressures and temperatures) are used to implement the aforesaid method, the *Antrodia cinnamomea* feed, the extract obtained at the top of the fractionating tank, the raffinate obtained at the bottom of the fractionating tank, the separated product 1 (F1), separated product 2 (F2), and separated product 3 (F3) are used to analyze and quantify the following properties: (1) total triterpenoids content in *Antrodia cinnamomea*, (2) total polysaccharides content in *Antrodia cinnamomea*, and (3) triterpenoids constituents and content in *Antrodia cinnamomea*.

Ursolic acid is used as a standard for the determination of total triterpenoids content (in mg/mL) based on absorbance at a wavelength of 548 nm. The phenol-sulfuric acid method is used for the determination of total polysaccharides content (in mg/mL), the amount of converted glucose is measured with absorbance at a wavelength 490 nm High-performance liquid chromatography quantitative analysis with a C18 tubular column is used for the measurement of individual constituent and content of the triterpenoids (in mg/mL). The experimental results are divided into two parts: (1) optimal separation and purification conditions for the functional components of *Antrodia cinnamomea*, and (2) the mass production process in separation and purification of the total triterpenoids content, total polysaccharides content, and individual triterpenoids. The results of the data analyses are shown in FIGS. 1 to 6.

First, the *Antrodia cinnamomea* feed is separated and the samples at the top and the bottom of the fractionating tank are collected. The contents are analyzed to calculate the K-value (mass distribution coefficient) of triterpenoids, K-value of polysaccharides, and the selectivity of the two K-values. The K-value of triterpenoids is calculated by the mass fraction of triterpenoids obtained from the top of the fractionating tank divided by that obtained from the bottom of the fractionating tank. Therefore, a K-value of triterpenoids of 1 indicates that the mass fractions of triterpenoids are the same in both the top and the bottom of the fractionating tank. A K-value of triterpenoids larger than 1 indicates that the *Antrodia cinnamomea* triterpenoids content is more likely to be separated at the top of fractionating tank. The K-value of polysaccharides can be calculated in a similar fashion, which equals to the mass fraction of polysaccharides obtained from the top of the fractionating tank divided by the amount of polysaccharides obtained from the bottom of the fractionating tank. When the K-value of polysaccharides is smaller than 1, it means that the *Antrodia cinnamomea* polysaccharides content is more likely to be separated at the bottom of the fractionating tank. Selectivity is defined as the ratio of K-value of triterpenoids to K-value of polysaccharides. By manipulating the operating pressures and temperatures, the separation efficiency of triterpenoids and polysaccharides of *Antrodia cinnamomea* can be changed.

Figure 2:
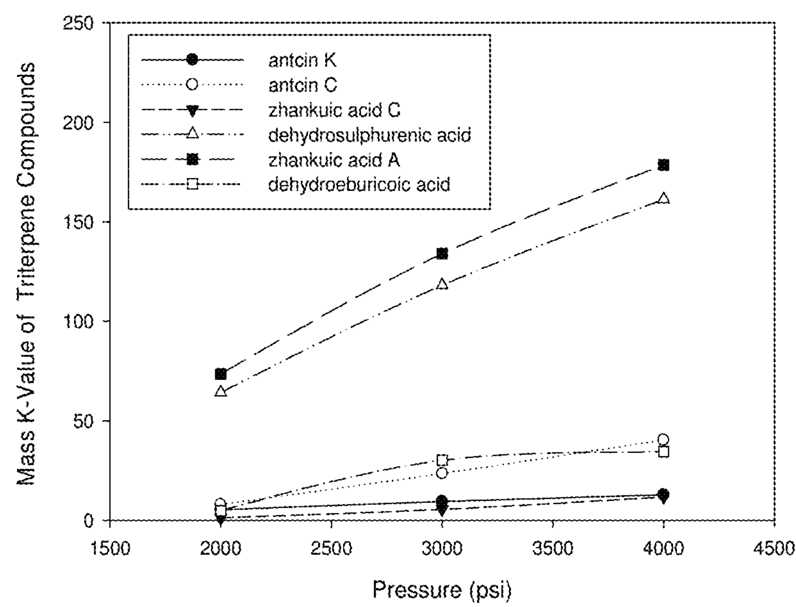
FIG. 2 is an analytic chart of pressure and K-value of *Antrodia cinnamomea* triterpenoid compounds of a preferred embodiment of the present invention.
Figure 3:
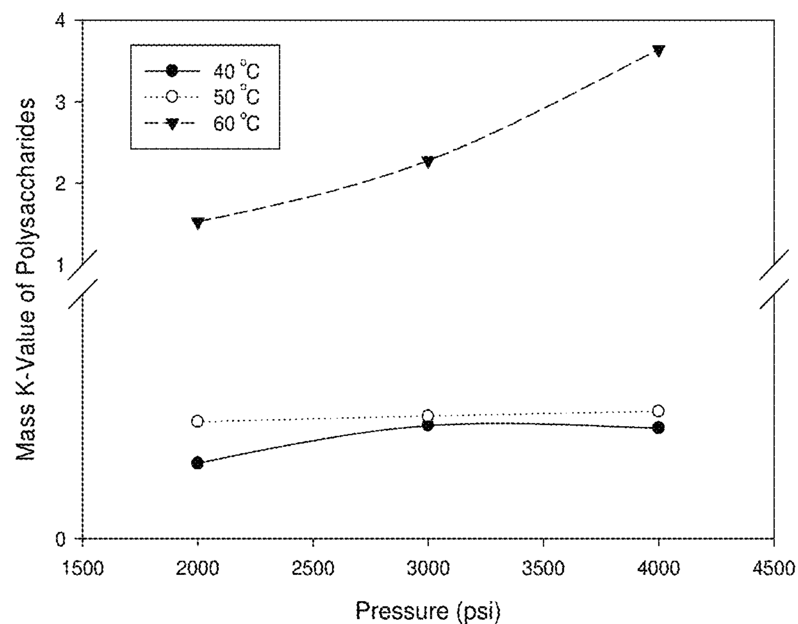
FIG. 3 is an analytic chart of pressure and K-value of *Antrodia cinnamomea* polysaccharides of a preferred embodiment of the present invention.

According to the numerical results after separation, as shown in FIG. 1, when the temperature is set at 40° C. and the pressure is set high (i.e., 4000 psi), the separation efficiency of total triterpenoids of *Antrodia cinnamomea* is approximately 50. The separation efficiency of each constituent of *Antrodia cinnamomea* triterpenoids in different pressure ranges (2000 to 4000 psi) is analyzed at an optimum temperature of 40° C. FIG. 2 shows the *Antrodia cinnamomea* triterpenoids under a pressure of 4000 psi, the separation efficiency of zhankuic acid A and dehydrosulphurenic acid is above 150, the separation efficiency of antcin C and dehydroeburicoic acid is above 30, and the separation efficiency of antcin K and zhankuic acid A is at least higher than 10. FIG. 3 shows when the temperature is set at 60° C. and the pressure is set high (i.e., 4000 psi), the separation efficiency of total polysaccharides of *Antrodia cinnamomea* is 3.6. In comparison, when the temperature is set at 40° C. and the pressure set at 4000 psi, the separation efficiency of total polysaccharides of *Antrodia cinnamomea* is only 0.23. Therefore, according to FIG. 1 and FIG. 3, a temperature of 40° C. and a pressure of 4000 psi are most suitable conditions for separating *Antrodia cinnamomea* triterpenoids at the top of the fractionating tank while the *Antrodia cinnamomea* polysaccharides is likely to be separated at the bottom of the fractionating tank.

Figure 4:
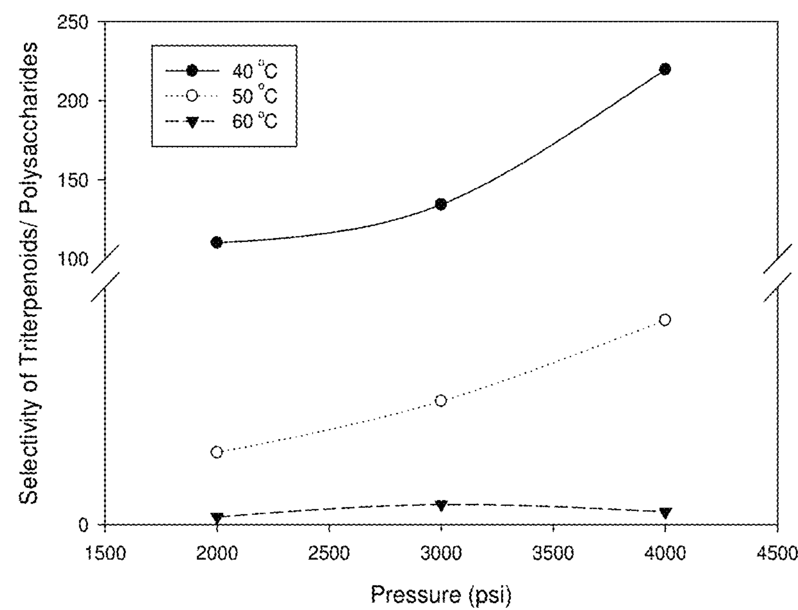
FIG. 4 is an analytic chart of pressure and selectivity of *Antrodia cinnamomea* triterpenoids and polysaccharides of a preferred embodiment of the present invention.
Figure 5:
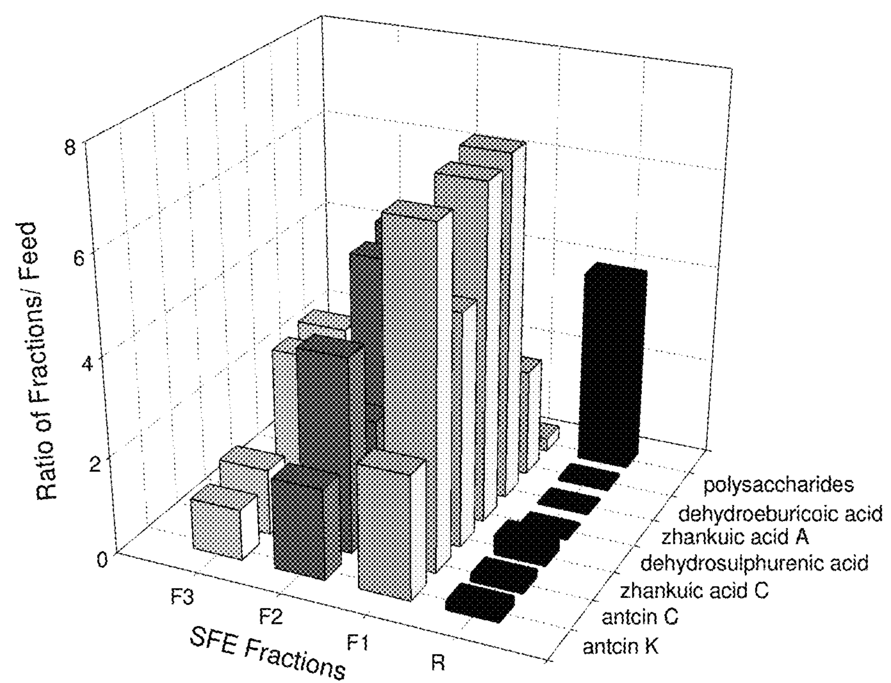
FIG. 5 is a chart of concentration profile of *Antrodia cinnamomea* triterpenoids and polysaccharides, fractionating tank bottom raffinate (R) and separating tanks F1, F2, and F3 of a preferred embodiment of the present invention.
Figure 6:
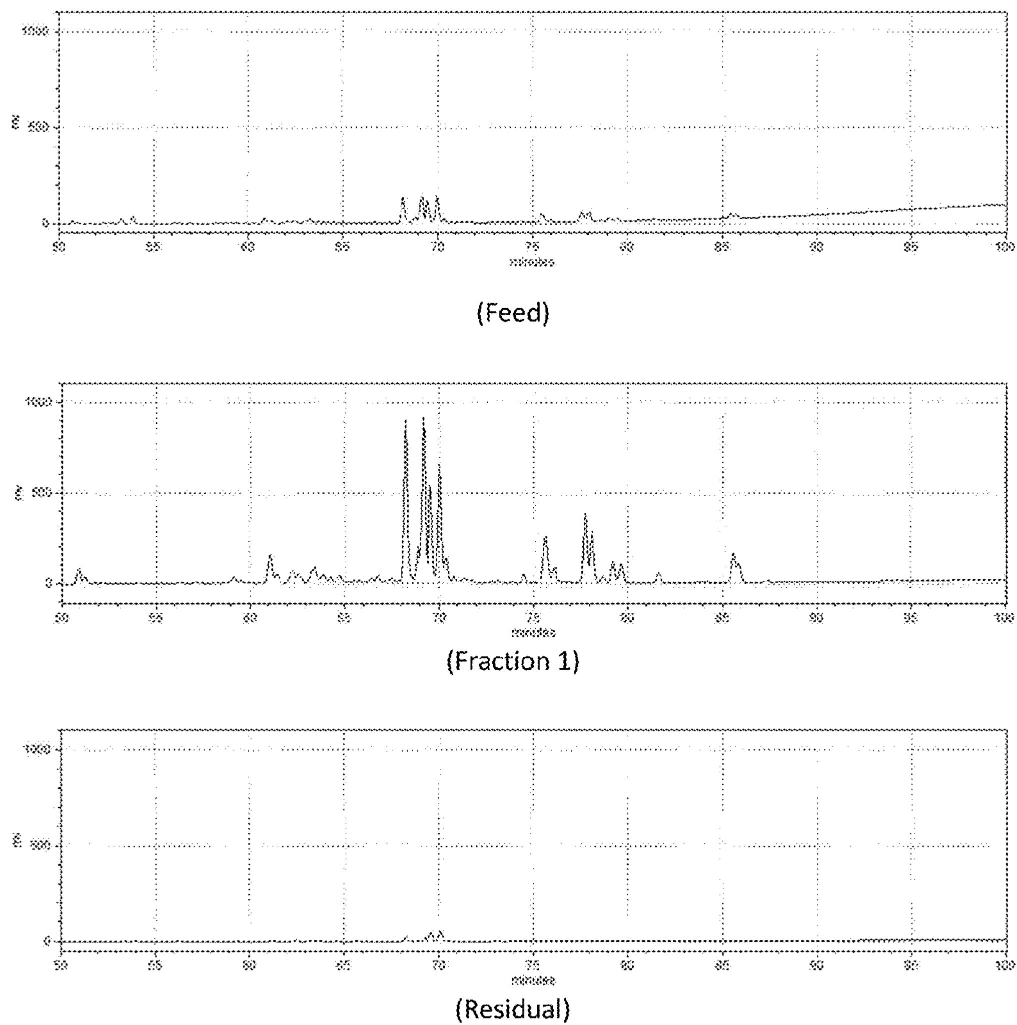
FIG. 6 is the high-performance liquid chromatography spectrum of a preferred embodiment of the present invention.

As shown in FIG. 4, when the temperature is set at 40° C. and the pressure is set at 4000 psi, the selectivity of triterpenoids and polysaccharides of *Antrodia cinnamomea* is 220, meaning that this operating condition is most suitable for purifying and separating the triterpenoids and polysaccharides from *Antrodia cinnamomea* in the three separating tanks (F1, F2, and F3). For example, in the operating conditions of a temperature of 40° C. and a pressure of 4000 psi, the triterpenoids of *Antrodia cinnamomea* are separated at the top of the fractionating tank, and then when the pressure is reduced (i.e., to 3000, 2000, 1000 psi in F1, F2, F3), the triterpenoids and polysaccharides content and the purity in *Antrodia cinnamomea* can be selectively separated, differentiated and purified. Therefore, as shown in FIG. 5, when the optimal experimental value of selectivity is used, the *Antrodia cinnamomea* feed is separated under the operating conditions of a temperature of 40° C. and a pressure of 4000 psi, the raffinate (R) is obtained at the bottom of the fractionating tank and the extract is obtained at the top of the fractionating tank. Then, the extract is separated in the three separating tanks F1, F2, and F3. FIG. 5 shows the distribution of concentrations of triterpenoids and polysaccharides in R, F1, F2, and F3. It shows that the polysaccharides constituent in *Antrodia cinnamomea* feed is being separated to R. Concurrently, the triterpenoids constituent of *Antrodia cinnamomea* feed is distributed to the separating tanks F1 and F2. The antcin C, dehydrosulphurenic acid, and zhankuic acid A of *Antrodia cinnamomea* triterpenoids are mostly being separated in F1. In addition, the triterpenoids constituents in *Antrodia cinnamomea* feed, F1, and R are compared. The HPLC spectrum shown in FIG. 6 demonstrated that after the triterpenoids of *Antrodia cinnamomea* feed are separated by the fractionating tank, more than 95% of triterpenoids can be separated and purified in the separated product 1 (F1).

As stated above, the method provided by the present invention which uses supercritical fluid technology to separate and purify the functional components of *Antrodia cinnamomea* can separate active constituents of triterpenoids and polysaccharides from the *Antrodia cinnamomea* feed. In comparison to the conventional methods of extracting and separating triterpenoids and polysaccharides from *Antrodia cinnamomea*, the present invention can separate *Antrodia cinnamomea* triterpenoids and polysaccharides simply by controlling the operating temperatures and pressures. There are no concerns for solvent residue and toxicity in the separation and purification processes. In addition, the present invention is based on an easy-to-understand calculation process of separation efficiency and selectivity of *Antrodia cinnamomea* triterpenoids and polysaccharides. The method of the present invention is easy to operate and can be scaled up for mass production and continuous operation. Therefore, the present invention is of high practical value.

What is claimed is:

1. A method to separate and purify functional components of *Antrodia cinnamomea* comprising:

mixing *Antrodia cinnamomea* powder and ethanol in a ratio of 1:5 to 10 (weight per volume);

centrifuging the mixture of *Antrodia cinnamomea* powder and ethanol so as to obtain a *Antrodia cinnamome* feed;

introducing the *Antrodia cinnamome* feed at a flow velocity of 1 L/hr to 3 L/hr into a fractionating tank at pressures of 2000 psi to 4000 psi and temperatures of 40° C. to 60° C. with a supercritical solvent of carbon dioxide/ethanol at a fluid flow velocity of 3 L/hr to 9 L/hr so as to extract triterpenoids of *Antrodia cinnamomea* from a top of the fractionating tank and polysaccharides of *Antrodia cinnamomea* from a bottom of the fractionating tank; and conveying the extracts of *Antrodia cinnamomea* and supercritical solvent continuously into three separating tanks at a temperature of 40° C. or 60° C. and reducing pressure stepwise from 3000 psi to 2000 psi and to 1000 psi so as to selectively increase the content and purity of the functional components of triterpenoids and polysaccharides and separate the solvent in a supercritical state.

2. The method defined in claim 1, wherein the *Antrodia cinnamomea* powder is the powder of the fruiting body, mycelium, dish culture, or solid culture of *Antrodia cinnamomea*.

3. The method defined in claim 1, wherein, under the operating conditions in the fractionating tank of a temperature set at 40° C. and a pressure set at 4000 psi, the selectivity of triterpenoids and polysaccharides of *Antrodia cinnamomea* is 220.

* * * * *